United States Patent
Goldstein

(10) Patent No.: US 7,892,242 B2
(45) Date of Patent: Feb. 22, 2011

(54) TOOL FOR REMOVING INTRAOCULAR FOREIGN BODIES

(75) Inventor: Burton G Goldstein, Tampa, FL (US)

(73) Assignee: University of South Florida, Tampa, FL (US)

( * ) Notice: Subject to any disclaimer, the term of this patent is extended or adjusted under 35 U.S.C. 154(b) by 912 days.

(21) Appl. No.: 11/306,432

(22) Filed: Dec. 28, 2005

(65) Prior Publication Data

US 2006/0212040 A1    Sep. 21, 2006

Related U.S. Application Data

(63) Continuation-in-part of application No. 10/711,226, filed on Sep. 2, 2004, now Pat. No. 7,326,220.

(60) Provisional application No. 60/481,322, filed on Sep. 2, 2003.

(51) Int. Cl.
*A61B 17/50* (2006.01)

(52) U.S. Cl. .................. 606/114; 606/110; 606/113; 606/127; 606/200

(58) Field of Classification Search ............. 606/107, 606/113, 114, 200, 127, 159, 110, 128
See application file for complete search history.

(56) References Cited

U.S. PATENT DOCUMENTS

| 6,280,451 | B1 * | 8/2001 | Bates et al. | 606/127 |
|---|---|---|---|---|
| 6,676,668 | B2 * | 1/2004 | Mercereau et al. | 606/127 |
| 2003/0135221 | A1 * | 7/2003 | Sabet | 606/107 |

* cited by examiner

*Primary Examiner*—Anhtuan T Nguyen
*Assistant Examiner*—Amy Lang
(74) *Attorney, Agent, or Firm*—Jeremy Spier; Ronald E. Smith; Smith & Hopen, P.A.

(57) ABSTRACT

A medical instrument captures and removes very large intraocular foreign bodies. The foreign bodies may have an irregular shape, a low coefficient of friction, and be made of non-magnetic materials. A fixed position hollow rod is mounted to a leading end of an elongate base and a lid is mounted to the distal end of the hollow rod. A control rod is slideably received within the hollow rod and a control knob slideably mounted on the elongate base is connected to the control rod to control extension and retraction of the control rod. A silicone basket depends from a rim formed at the distal end of the control rod. A silicone wire interconnects the hollow rod and a bottom of the basket so that the basket is drawn parallel to the control rod when the control rod is extended. The lid covers the basket when the control rod is retracted.

3 Claims, 3 Drawing Sheets

TOOL FOR REMOVING INTRAOCULAR FOREIGN BODIES

CROSS-REFERENCE TO RELATED DISCLOSURES

This disclosure is a continuation-in-part of an earlier disclosure of the same title filed on Sep. 2, 2004, Ser. No. 10/711,226, which earlier disclosure claims priority from U.S. provisional application Ser. No. 60/481,322, entitled: "Intraocular Foreign Body Basket," filed Sep. 2, 2003. Both of said earlier disclosures are hereby incorporated into this disclosure by reference.

BACKGROUND OF THE INVENTION

1. Field of the Invention

This invention relates, generally, to surgical tools. More particularly, it relates to a surgical tool used by retina specialists for extracting intraocular foreign bodies.

2. Description of the Prior Art

The foreign body extractors in common use typically include opposed jaws that operate as forceps. A well-known tool, known as a vitreoretinal forceps, has a stainless steel construction, a serrated plastic handle, and is autoclavable. The jaws may be smooth or serrated, and they may open horizontally or vertically.

Another well-known instrument is the Katena® "squeeze handle" forceps. These tools include light-in-weight titanium handles. The shanks are 20 gauge and the front ends are formed of hardened stainless steel to enhance grasping. The jaws may open horizontally, vertically, or the jaws may have a 45° angle formed therein. The jaws having the 45° angle are known as membrane peeling forceps.

Forceps are limited in that the "bite size" may be too small to remove relatively large foreign objects. Moreover, an object having an irregular shape is often hard to capture using a forceps-type tool. A smooth (low coefficient of friction), non-magnetic object like smooth glass or a BB is also hard to capture using a forceps.

The prior art device most relevant to the present disclosure is disclosed in the incorporated disclosures. In the incorporated disclosures, the forceps of the prior art are eschewed in favor of a flexible mesh basket that is fully open when extended relative to a handle and fully closed when retracted into the handle.

One drawback of the earlier device is that it is difficult to manufacture a flexible, cinchable basket. Still, the highly novel concept of a basket, as distinguished from the jaws of a forceps, has many advantages. The diameter of the basket, for example, may be up to 6 mm, thereby enabling the removal of objects larger than any object retrievable by a conventional forceps. Moreover, objects having irregular shapes and objects having smooth, low coefficient of friction or non-magnetic surfaces are capturable by a basket.

What is needed, then, is a tool for removing intraocular foreign bodies that incorporates a basket that is not difficult to manufacture so that the benefits of a basket-based tool may be economically realized.

However, in view of the prior art considered as a whole at the time the present invention was made, it was not obvious to those of ordinary skill in the medical arts how the needed tool could be provided.

SUMMARY OF INVENTION

The long-standing but heretofore unfulfilled need for a tool adapted to remove small to very large intraocular foreign bodies, including such bodies having irregular shapes, formed of non-magnetic materials, and having smooth, low coefficient of friction surfaces is now met by a new, useful, and non-obvious invention.

The novel surgical tool for capturing and removing intraocular foreign bodies includes an elongate, generally cylindrical, hollow base that is gripped by a user. The leading end of the cylindrical base is frusto-conical, i.e., it tapers down in diameter from the diameter of the cylindrical base to the diameter of a rigid hollow rod. The rigid hollow rod has a fixed, immovable position and it terminates at its distal free end in a flat, circular lid. An elongate control rod is slideably mounted in the lumen of the hollow rod. An elongate slot is formed in the base and a slideably mounted control plate covers the slot. The control plate is apertured to enable interconnection of the elongate control rod and a control knob that surmounts the control plate. Accordingly, thumb-controlled movement of the control knob in a proximal-to-distal direction causes extension of the elongate control rod and distal-to-proximal travel of the control knob causes retraction of the hollow rod. A circular rim is mounted to the distal end of the elongate control rod and a basket, preferably formed of an elastic silicone, depends from the rim. An articulating wire, also formed of an elastic silicone, interconnects a bottom of the basket and the rigid hollow rod. Full retraction of the elongate control rod brings the basket rim into juxtaposition with the flat, circular lid formed at the distal end of the rigid hollow rod, thereby preventing spillage from the basket of any object therein. Partial extension of the elongate control rod positions the basket in a position where its axis of symmetry is perpendicular to the axis of symmetry of the elongate control rod and in such position the basket is fully open and useable to retrieve intraocular objects. Further extension of the elongate control rod pulls the bottom of the basket toward the elongate control rod and full extension brings the basket into parallelism with the elongate control rod. The instrument is introduced into the eye when the elongate control rod is in said fully extended position. The basket is then placed into the aforesaid perpendicular orientation to retrieve an intraocular object. The basket is then again brought into the parallel position to facilitate withdrawal of the basket from the eye. The elongate control rod is then fully retracted to cover the basket with the flat, circular lid.

More particularly, the novel instrument for capturing and removing intraocular foreign bodies includes an elongate base adapted to be held in a human hand. The elongate base has a hollow interior. An elongate control rod has a proximal end slideably disposed in the hollow interior of the elongate base and has a distal end that extends distally of the elongate base.

A control knob is connected to the elongate control rod. The control knob is slideably mounted on the elongate base for controlling the instantaneous position of the elongate control rod.

A rim is mounted to a distal free end of the elongate control rod and a basket made of a flexible material is mounted in depending relation to the rim. The basket is adapted to capture and remove a foreign body from a patient's eye.

A user controls the position of the control rod and hence the basket by displacing the control knob relative to the elongate base.

An elongate control slot is formed in the elongate base and the elongate control rod is connected to the control knob through the elongate control slot. An elongate control plate covers the elongate control slot and is slideably mounted with respect to the elongate base. An aperture formed in the elongate control plate to enable interconnection of the control knob and the elongate control rod.

An elongate hollow rod is mounted to a leading end of the base. A closure means for the basket is mounted to a distal end of the elongate hollow rod. The elongate hollow rod and therefore the closure means are mounted to the distal end of the elongate base in a plane slightly above a plane occupied by the rim so that displacement of the control knob in a distal-to-proximal direction positions the basket directly below the closure means so that a foreign object in the basket is retained therein by the closure means.

The rim has a circular configuration and the closure means has a flat, disc shape and a size corresponding to the rim so that the basket is closed at its mouth when the closure means is in registration with the rim.

A flexible connector is disposed in interconnecting relation to a bottom of the basket and the hollow rod. The instrument has a position of repose when the flexible connector is taut. The basket has a longitudinal axis of symmetry disposed normal to a longitudinal axis of symmetry of the hollow rod when the instrument is in the position of repose. The instrument has a position of full retraction when the flexible connector is slack and the rim of the basket is in juxtaposition with the closure means. The instrument has a position of full extension when the flexible connector is taut. The basket has a longitudinal axis of symmetry disposed parallel to a longitudinal axis of symmetry of the hollow rod when the instrument is in the position of full extension.

The invention accordingly comprises the features of construction, combination of elements, and arrangement of parts that will be exemplified in the description set forth hereinafter and the scope of the invention will be indicated in the claims.

BRIEF DESCRIPTION OF THE DRAWINGS

For a fuller understanding of the nature and objects of the invention, reference should be made to the following detailed description, taken in connection with the accompanying drawings, in which.

DETAILED DESCRIPTION OF THE PREFERRED EMBODIMENT

Figure 1:
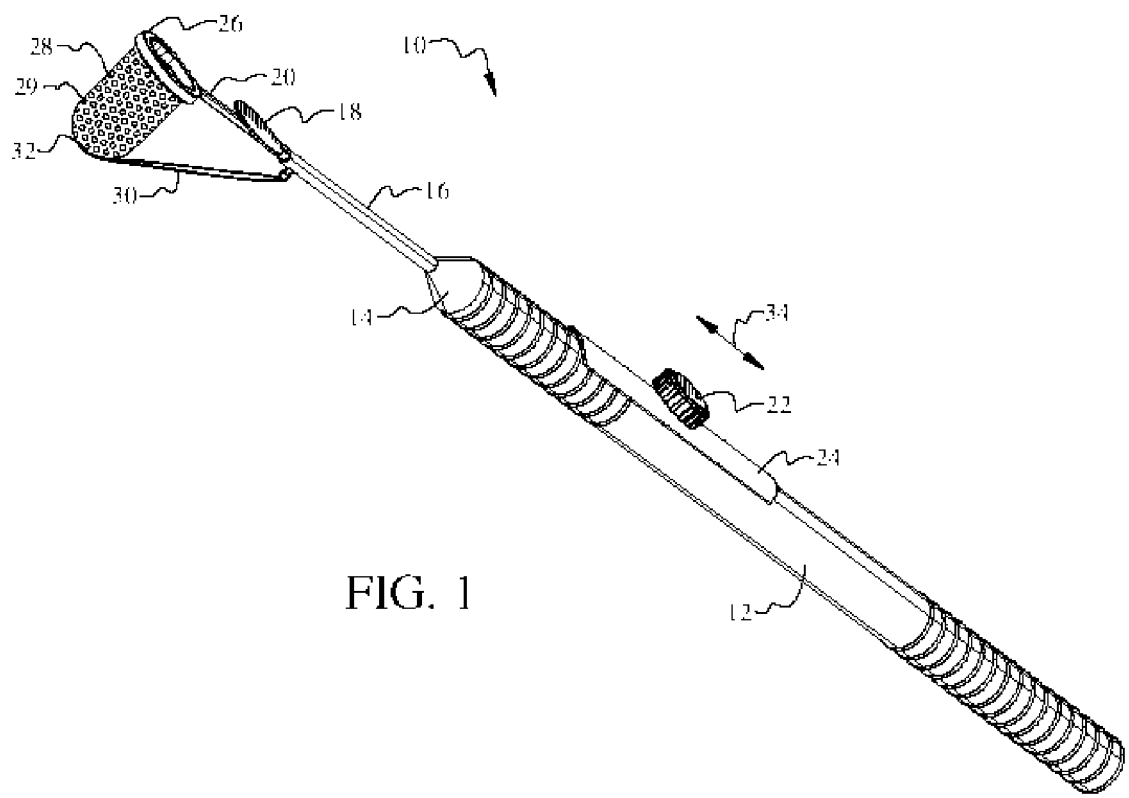
FIG. 1 is a perspective view of the novel instrument when the basket is fully retracted and therefore covered by the fixed-position lid.
Figure 2:
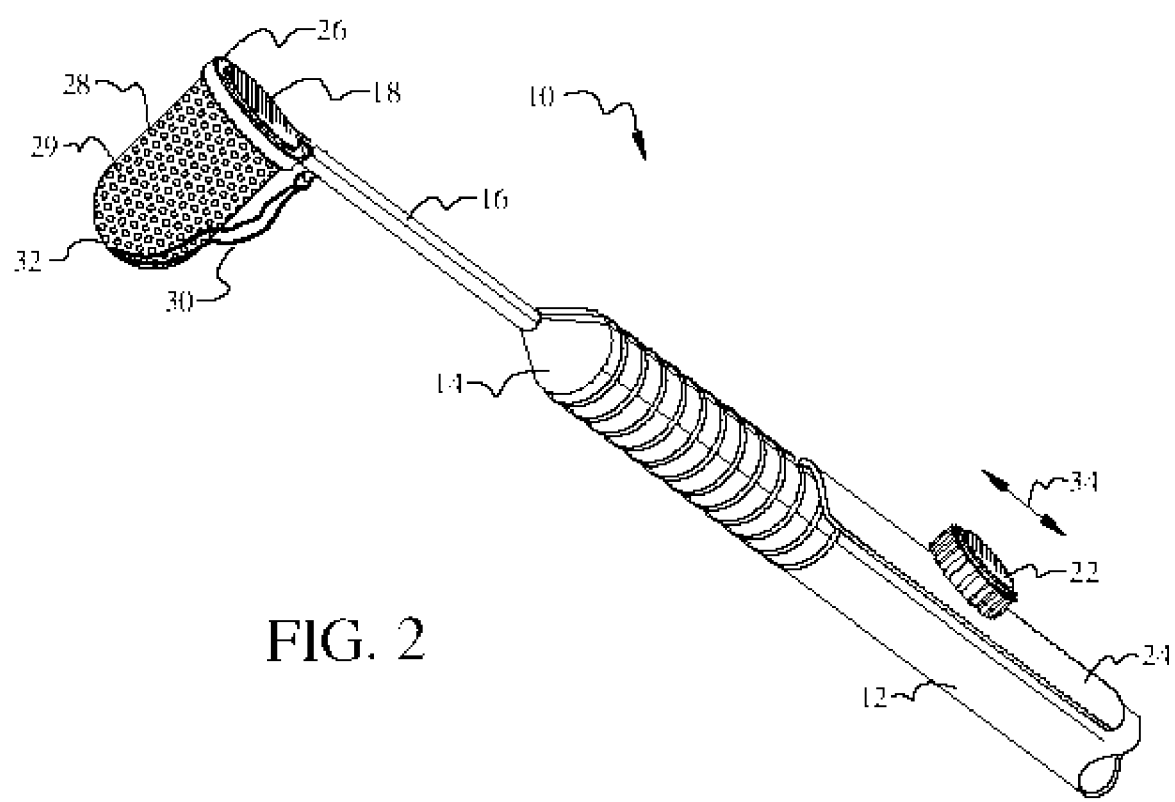
FIG. 2 is a perspective view where the basket is extended away from the lid in a fully open configuration.
Figure 3:
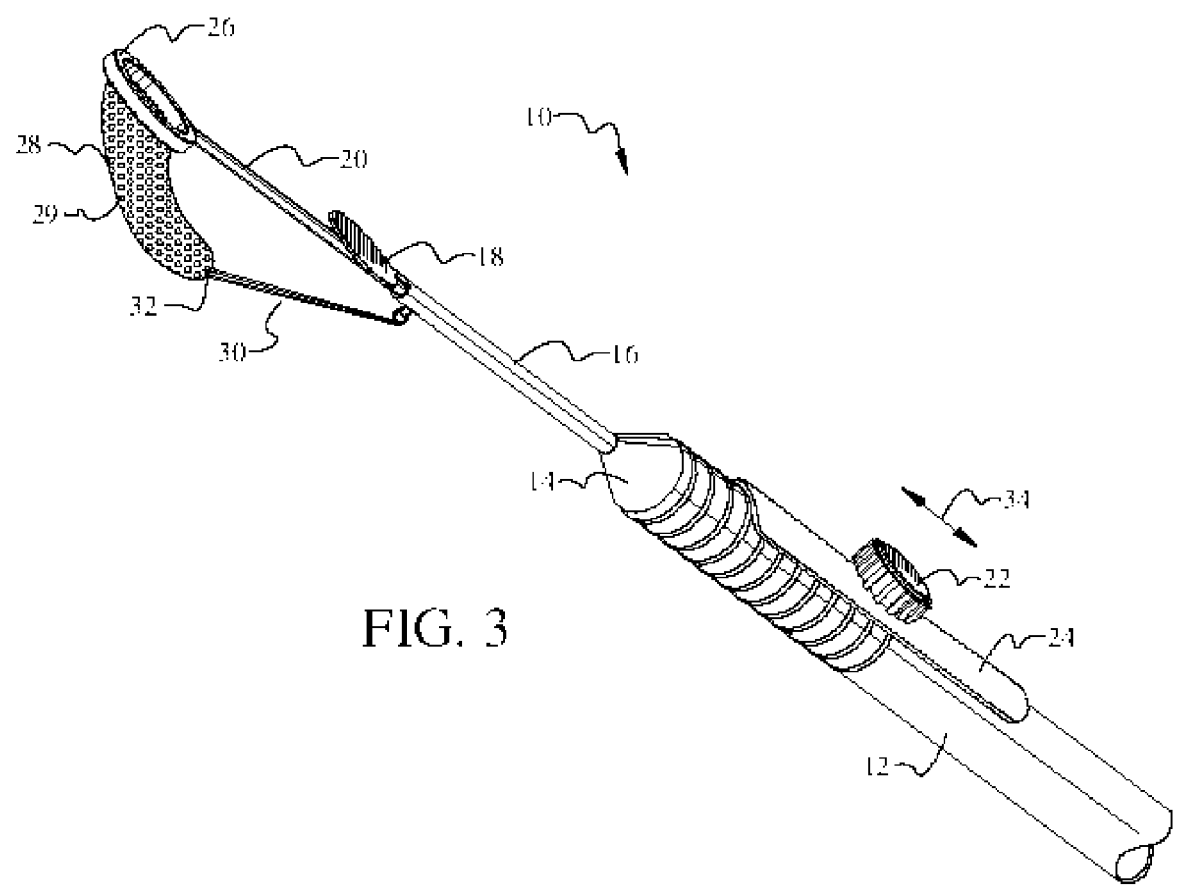
FIG. 3 is a perspective view where the basket is extended still further from the lid so that the basket is substantially closed to capture a foreign object therein.

Referring now to FIGS. 1-3, it will there be seen that an illustrative embodiment of the invention is denoted as a whole by the reference numeral 10.

Novel intraocular foreign body extractor 10 includes elongate base 12 that is sized for comfortable holding in a human hand. Base 12 is cylindrical along its extent but its leading 14 is frusto-conical in configuration, i.e., said leading end tapers downwardly in diameter from the diameter of the cylindrical base to the diameter of hollow rod 16.

A flat, circular, basket closure means or lid 18 is formed integrally with hollow rod 16 at the distal free end thereof. Rod 16 and hence lid 18 have a fixed position and are not movable relative to base 12.

Hollow rod 16 has a lumen that slideably receives elongate control rod 20 therein. The proximal end of elongate control rod 20 is disposed within the interior of base 12 and is mechanically connected by any suitable means to control knob 22. An elongate slot formed in base 12 enables a user to slide control knob 22 from a trailing (proximal) end of the elongate slot to the leading (distal) end thereof and any point therebetween. In this particular embodiment, elongate sliding plate 24 covers the elongate slot so that dirt or other debris cannot enter into the interior of base 12.

Control rod 20 terminates at its distal end in a circular rim 26 that is made of the same metallic material as said control rod. Thus, circular rim 26 is not cinchable as is the rim of the device disclosed in the incorporated disclosures. Accordingly, instrument 10 is provided in a series of models where the diameter of rim 26 varies between models so that a user may select a rim of small diameter or a rim of a larger diameter, up to about 6 mm in diameter for the largest rim.

Basket 28 is mounted to rim 26 and depends therefrom. Basket 28 is made of a flexible material, preferably elastic silicone. Metallic rim 26 is covered by the elastic silicone that forms basket 28, thereby forming a permanent attachment. A plurality of equidistantly spaced fenestrations, collectively denoted 29, are formed in basket 28 as depicted.

A flexible connector, in the form of articulating wire 30, also made of elastic silicone, has a proximal end pivotally connected to fixed position hollow rod 16 and a distal end hingedly connected to bottom 32 of basket 28.

The FIG. 1 position may be thought of as the position of repose because basket 28 is fully open, i.e., the longitudinal axis of symmetry of basket 28 is normal to the longitudinal axis of symmetry of hollow rod 16 and elongate control rod 20. Silicone elastic control wire 30 is substantially taut, i.e. there is substantially no slack in said wire.

When control knob 22 is in its fully retracted position at the trailing end of the covered elongate slot, as depicted in FIG. 2, the mouth of basket 28 is fully covered by lid 18. The user may then carry tool 10 to any desired location where the retrieved foreign object is to be removed from basket 28. Moving control knob 22 in a proximal-to-distal (trailing-to-leading) direction positions basket 28 in the FIG. 1 position where the basket can be emptied.

Extending control knob 22 to the FIG. 3 position causes bottom 32 of basket 28 to approach control rod 20. Fully extending control knob 22 to its forwardmost position relative to elongate base 12 pulls bottom 32 of basket 28 close to said elongate control rod 20 and effectively positions basket 28 into substantially parallel relation to said elongate control rod 20. Note that this collapses the basket so that any foreign object therein cannot escape therefrom.

Figure 4:
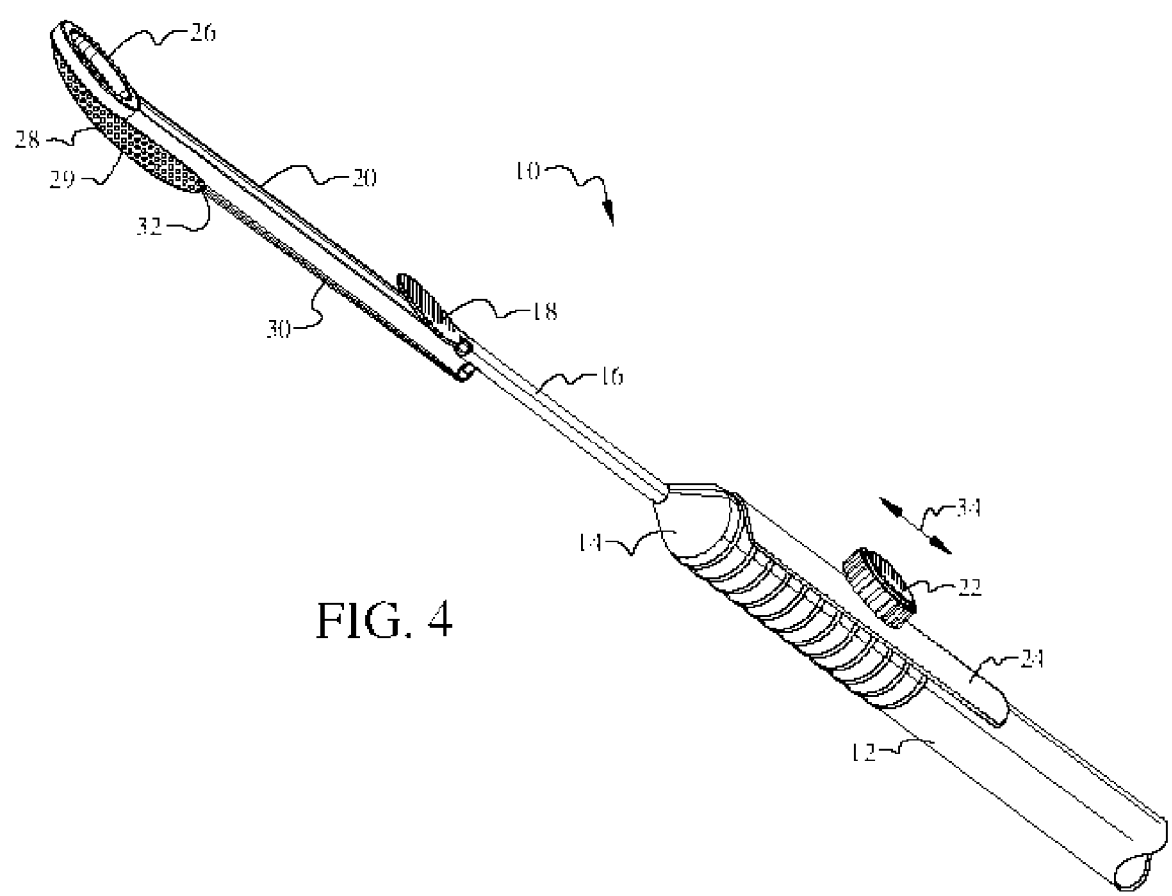
FIG. 4 is a perspective view where the basket is fully extended so that the basket is fully closed to capture a foreign object therein.

Instrument 10 is introduced into and removed from the eye, through the corneal-scleral wound, when in the FIG. 4 position.

Base 12 is preferably formed of a rigid metallic material although it may also be formed of plastic or any other suitable material.

Control knob 22 controls the instantaneous position of elongate control rod 20 and hence of rim 26 and basket 28. Control knob 22 is slideably mounted for movement along the extent of the slot covered by sliding control plate 24 as indicated by double-headed directional arrow 34 in all of the Figures. A thumb of a user easily engages control knob 22 when tool 10 is held in a user's palm, supported by the fingers of the user.

Tool 10 enables a surgeon to remove even very large intraocular foreign bodies through a small incision. Elongate base 12 is not introduced into the incision. Rim 26 and net 28 are fully inserted through the incision with net 28 in its FIG. 4 position. Control knob 22 is then retracted until basket 28 reaches its FIG. 1 position. This enables the physician to capture very large intraocular bodies in said net. The foreign body or bodies are captured in the net when the net is returned to its FIG. 4 position. Upon removal of the basket from the eye, the instrument is placed into its FIG. 2 position for transporting the foreign object to a disposal location if no forensic study is required or to an examination location if a forensic study is required.

It will be thus be seen that the objects set forth above, and those made apparent from the foregoing description, are efficiently attained and since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention that, as a matter of language, might be said to fall therebetween. Now that the invention has been described,

What is claimed is:

1. An instrument for capturing and removing intraocular foreign bodies, comprising:
    an elongate base adapted to be held in a human hand, said elongate base having a hollow interior;
    an elongate control rod having a proximal end slideably disposed in said hollow interior of said elongate base and having a distal end that extends distally of said elongate base;
    a control knob connected to said elongate control rod;
    said control knob being slideably mounted on said elongate base for controlling the instantaneous position of said elongate control rod;
    an elongate control slot formed in said elongate base;
    said elongate control rod being connected to said control knob through said elongate control slot;
    a rim of circular configuration mounted to a distal free end of said elongate control rod;
    a basket made of a flexible material mounted in depending relation to said rim, said basket having an open mouth that encircles said rim, and a closed end positioned below said rim;
    an elongate hollow rod fixedly secured to a leading end of said base;
    a closure means for said basket fixedly secured to a distal end of said elongate hollow rod;
    said closure means being in a fixed, immovable position at said distal end of said elongate hollow rod in a plane slightly above a plane occupied by said rim;
    said closure means being flat, having a disk shape, and having a diameter substantially equal to a diameter of said rim so that said open mouth of said basket is closed when said closure means overlies said rim;
    a flexible connector disposed in interconnecting relation to a bottom of said flexible material and a distal end of said hollow rod;
    said control knob and said elongate control rod having a first position where said rim is in a first position distal to said closure means and said basket is in a position of repose where said flexible material depends straight down from said rim and where said flexible connector forms a straight line from said distal end of said hollow rod to said bottom of the flexible material;
    said control knob and said elongate control rod having a fully retracted position where said rim underlies said closure means, said basket being in said position of repose and said flexible connector being in a collapsed, non-taut configuration substantially perpendicular to said elongate control rod;
    said control knob and said elongate control rod having a fully extended position where said rim is distal to said first position of said rim, said flexible connector is taut and substantially parallel to said elongate control rod, and where said flexible material of said basket that depends from said rim when in repose is disposed substantially parallel to said rim and to said elongate control rod;
    said elongate hollow rod and said closure means having respective fixed positions unaffected by retraction and extension of said control knob and said elongate control rod; and
    whereby said instrument is adapted to capture and remove a foreign body from a patient's eye.

2. The instrument of claim 1, further comprising:
    an elongate control plate for covering said elongate control slot;
    said elongate control plate being slideably mounted with respect to said elongate base; and
    an aperture formed in said elongate control plate to enable interconnection of said control knob and said elongate control rod.

3. The instrument of claim 1, further comprising:
    a plurality of equidistantly spaced fenestrations formed in said basket.

* * * * *